United States Patent
Feng et al.

(10) Patent No.: US 11,774,455 B2
(45) Date of Patent: Oct. 3, 2023

(54) PEPTIDE APTAMER FOR SPECIFIC RECOGNITION OF ARGININE AND ITS APPLICATION

(71) Applicant: INSTITUTE OF SUBTROPICAL AGRICULTURE, CHINESE ACADEMY OF SCIENCES, Changsha (CN)

(72) Inventors: Zemeng Feng, Changsha (CN); Yumin He, Changsha (CN); Lei Deng, Changsha (CN); Zhong Cao, Changsha (CN); Zhongliang Xiao, Changsha (CN); Yulong Yin, Changsha (CN)

(73) Assignee: INSTITUTE OF SUBTROPICAL AGRICULTURE, CHINESE ACADEMY OF SCIENCES, Changsha (CN)

( * ) Notice: Subject to any disclaimer, the term of this patent is extended or adjusted under 35 U.S.C. 154(b) by 564 days.

(21) Appl. No.: 17/052,173

(22) PCT Filed: Nov. 16, 2019

(86) PCT No.: PCT/CN2019/119036
§ 371 (c)(1),
(2) Date: Oct. 30, 2020

(87) PCT Pub. No.: WO2021/003945
PCT Pub. Date: Jan. 14, 2021

(65) Prior Publication Data
US 2022/0260582 A1    Aug. 18, 2022

(30) Foreign Application Priority Data
Jul. 5, 2019   (CN) .......................... 201910604881.0

(51) Int. Cl.
G01N 33/68    (2006.01)
G01N 33/533   (2006.01)
G01N 33/53    (2006.01)

(52) U.S. Cl.
CPC ....... G01N 33/6812 (2013.01); G01N 33/533 (2013.01)

(58) Field of Classification Search
CPC ............... G01N 33/533; G01N 33/532; G01N 33/6812
See application file for complete search history.

(56) References Cited

U.S. PATENT DOCUMENTS

2015/0292005 A1* 10/2015 Tomita .................. C12N 15/111
                                                                506/9

FOREIGN PATENT DOCUMENTS

| CN | 110220960 A | 9/2019 |
| CN | 110220961 A | 9/2019 |
| CN | 110257388 A | 9/2019 |
| CN | 110426435 A | 11/2019 |
| KR | 20180045191 A | 5/2018 |

OTHER PUBLICATIONS

Yaun et al. An aptamer-based fluorescence bio-sensor for chiral recognition of arginine enantiomers. Spectrochimica Acta Part A: Molecular and Biomolecular Spectroscopy 2018, vol. 200, pp. 330-338. (Year: 2018).*

Yuan Haiyan et al."An Aptamer-based Fluorescence Probe for Chiral Recognition of Arginine Enantiomers" Spectroscopy and Spectral Analysis, vol. 38, No. 10, Oct. 31, 2018(Oct. 31, 2018), pp. 253 and 254.

* cited by examiner

*Primary Examiner* — Shafiqul Haq
(74) *Attorney, Agent, or Firm* — Bayramoglu Law Offices LLC

(57) ABSTRACT

A peptide aptamer for specific recognition of arginine and its application are provided. The sequence of the peptide aptamer is shown in SEQ ID No. 1. The peptide aptamer is modified by a group that improves stability, or by a fluorescent group, an isotope and an electrochemical group that provide a detection signal, or by an affinity ligand and a mercapto. According to the computer-aided molecular docking simulation prediction, the peptide aptamer that can specifically bind to L-arginine is screened, which is verified by an isothermal titration calorimeter. The peptide aptamer has the advantages of good stability, strong binding ability, high specificity and low production cost.

2 Claims, 1 Drawing Sheet

Specification includes a Sequence Listing.

PEPTIDE APTAMER FOR SPECIFIC RECOGNITION OF ARGININE AND ITS APPLICATION

CROSS REFERENCE TO THE RELATED APPLICATIONS

This application is the national phase entry of International Application No. PCT/CN2019/119036, filed on Nov. 16, 2019, which is based upon and claims priority to Chinese Patent Application No. 201910604881.0, filed on Jul. 5, 2019, the entire contents of which are incorporated herein by reference.

TECHNICAL FIELD

The present invention relates to the intersection of biophysics, biochemistry, molecular biology and analytical chemistry, and in particular to a peptide aptamer for specific recognition of arginine and its application.

BACKGROUND

L-arginine is one of the basic components of protein. It participates in the ornithine cycle in animals, promotes the formation of urea, and transforms ammonia produced in the human body into non-toxic urea through the ornithine cycle, which is excreted in the urine, thus reducing blood ammonia concentration. In addition, L-arginine contributes to maintaining the electrical properties of proteins in vivo and is a basic amino acid-like lysine. In recent years, some studies have shown that L-arginine can be used as an important disease-related biomarker. Because succinate synthase in patients with hepatocellular carcinoma cannot be synthesized, the concentration of L-arginine in vivo is often low. In addition, L-arginine is also an indicator of nutritional status in animal and plant tissues. When the nutritional status is abnormal, the content of L-arginine also shows different levels. Like other amino acids, L-arginine is an important indicator to measure the level of nutritional value in food.

At present, there are two main methods for arginine analysis: (i) using large-scale instruments for detection, such as liquid chromatography, amino acid analyzer, nuclear magnetic resonance instrument, etc., but this kind of method requires not only expensive instrument investment, but also highly professional operators to operate, and the pre-treatment is complex; (ii) using enzyme-based biosensor for detection, which is easy to operate and low in cost, but the low stability and high production cost of enzyme limit its development. Therefore, it is significant to establish a low-cost, easy-to-operate, stable and fast biosensor method to detect arginine, and a peptide aptamer for specific recognition of L-arginine can meet the demand.

SUMMARY

The present invention aims to overcome the shortcomings of the prior art and provide a peptide aptamer for specific recognition of arginine and its application.

For the purpose mentioned above, the technical scheme provided by the present invention is as follows.

A sequence of the peptide aptamer for specific recognition of the arginine is shown in SEQ ID No.1: FGHIHEGY (F: phenylalanine; G: glycine; H: histidine; I: isoleucine; E: glutamic acid; Y: tyrosine).

Preferably, the peptide aptamer can be modified by a group that improves stability, or by a fluorescent group, an isotope, an electrochemical group, etc., which provide a detection signal, or by an affinity ligand, a mercapto, etc.

The peptide aptamer can be used to prepare an arginine detection kit, an arginine test paper or an arginine detection biosensor.

The present invention is further described as follows.

In the present invention, a primary sequence of an L-arginine sensing protein which can be recognized with L-arginine is obtained by searching for the L-arginine sensing proteins and transporters from a protein library, followed by cutting the primary sequence of the L-arginine sensing protein into 8 amino acid residues to obtain a peptide library and removing repeated peptide sequences from the peptide library. Next, a molecular simulation is performed on the peptides in the deduplicated peptide library and L-arginine to obtain a peptide aptamer library that can specifically bind to the arginine, and preferably, the peptide aptamer library is selected for experimental verification. Then, a binding verification is carried out on the peptide aptamer library and the arginine by an isothermal titration calorimeter. A verification method is as follows: 1 µM of the L-arginine is titrated with 10 µM of the peptide aptamer, a solvent and a binding buffer is 10 mM PBS buffer, pH is 7.4, and a binding temperature is 37° C., and the peptide aptamer that can specifically bind to the L-arginine can be determined.

In the present invention, the sequence of the peptide aptamer that can specifically bind to the L-arginine is shown in SEQ ID No.1, which is confirmed based on the molecular docking simulation and the binding verification by the isothermal titration calorimeter, wherein the sequence from left to right is N-terminal to C-terminal, and letters of the sequence are single-letter abbreviations of amino acids.

The peptide aptamer that can specifically bind to the L-arginine is provided based on the molecular docking simulation and the binding verification by the isothermal titration calorimeter in the present invention, and its sequence is shown in SEQ ID No.1. The screening process is faster and more convenient than the general phage display, synthesis of random peptide library and other methods. It does not need a lot of manpower and material resources, and it provides a bio-recognition element with good stability, high sensitivity, low cost, simple preparation and easy modification for the rapid detection of the L-arginine and the development of a biosensor. Compared with arginine aptamers in the prior art, the peptide aptamer for specific recognition of the arginine obtained by the present invention has a stronger binding force, which is more suitable for drug development and use as a detection reagent, and has low synthesis cost.

DETAILED DESCRIPTION OF THE EMBODIMENTS

Molecular simulation and binding verification of a peptide aptamer with L-arginine A) Molecular simulation of the peptide aptamer and the L-arginine: AutoDock is used to place the L-arginine on the active site of the peptide aptamer, and its binding mode is predicted. The predicted binding parameters of the L-arginine and the peptide aptamer is obtained, and the binding energy is −3.82 kcal/mol. While other amino acids having a similar structure to the L-arginine have no binding ability with the peptide aptamer.

Figure 1:
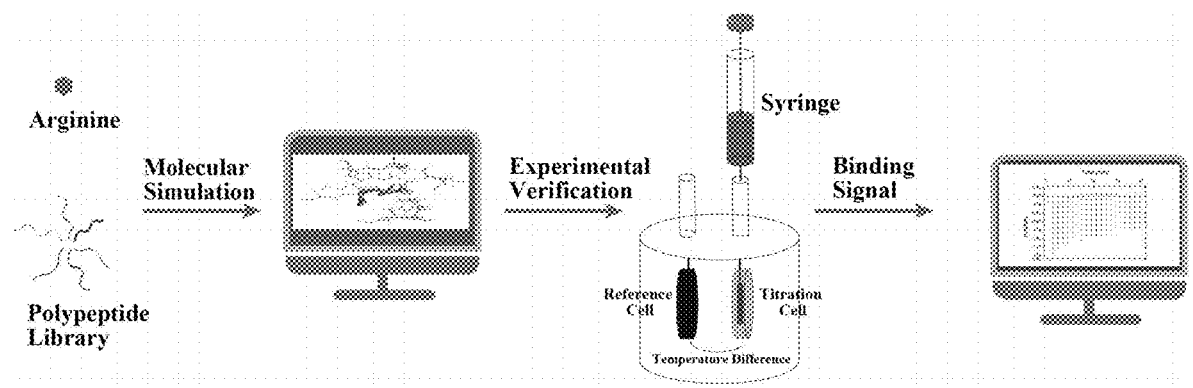
FIG. 1 is a flow chart showing prediction and screening of a peptide aptamer-based on a molecular docking simulation.
Figure 2:
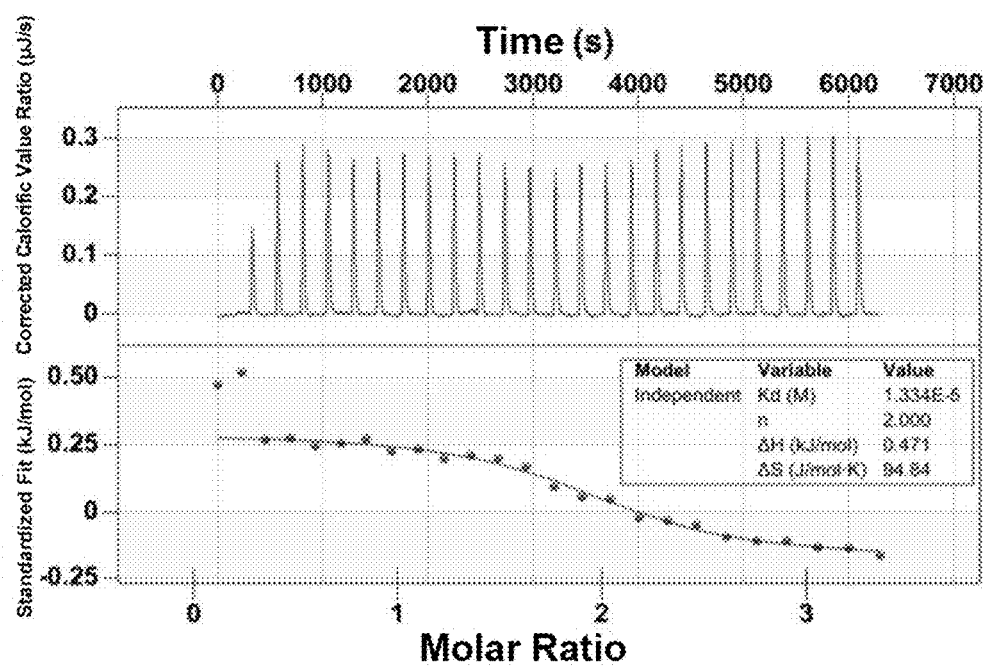
FIG. 2 is a diagram showing a data simulation result of a binding verification of the peptide aptamer of the present invention with L-arginine.

B) Binding verification of the simulated peptide aptamer with the L-arginine by the isothermal titration calorimeter C) The sequence of the peptide aptamer used in the binding verification is shown in SEQ ID No.1. A solution with a concentration of 10 μM is prepared by 10 mM PBS. 100 μL of the solution is put into a syringe of the isothermal titration calorimeter (FIG. 1), and 360 μL of 1 μM L-arginine is added to a titration cell for titration. The temperature is set at 37° C., and 25 drops are titrated with each drop of 4 μL. The results of the binding verification are shown in FIG. 2. The results show that the binding parameter Kd value of the peptide aptamer and the L-arginine is $1.334 \times 10^{-5}$ M. The isotherm titration calorimeter is used to determine that the peptide aptamer has no or very weak binding ability to other amino acids having a similar structure to the L-arginine.

What is claimed is:

1. A peptide aptamer for specific recognition of arginine, the peptide aptamer consisting of the amino acid sequence as set forth in SEQ ID No. 1.

2. An arginine detection kit comprising: an arginine test paper comprising the peptide aptamer according to claim 1 or an arginine detection biosensor comprising the peptide aptamer according to claim 1.

\* \* \* \* \*

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: The sequence is synthetized.

<400> SEQUENCE: 1

Phe Gly His Ile His Glu Gly Tyr
1               5
```